United States Patent [19]
Barner et al.

[11] Patent Number: 5,986,066
[45] Date of Patent: Nov. 16, 1999

[54] BIOSENSORY LAYERS

[75] Inventors: Richard Barner, Witterswil; Walter Huber, Kaiseraugst; Josef Hübscher, Nunningen; Jürg Hurst, Basel; Daniel Schlatter, Oberwil, all of Switzerland

[73] Assignee: Roche Diagnostics Corporation, Indianapolis, Ind.

[21] Appl. No.: 08/878,105

[22] Filed: Jun. 18, 1997

Related U.S. Application Data

[63] Continuation of application No. 08/492,257, Jun. 22, 1995, abandoned, which is a continuation of application No. 08/085,716, Jun. 30, 1993, abandoned.

[30] Foreign Application Priority Data

Jul. 10, 1992 [CH] Switzerland ............... 2178/92

[51] Int. Cl.$^6$ ............ C07K 16/00; G01N 33/543; G01N 33/547
[52] U.S. Cl. ............ 530/391.1; 436/501; 436/512; 436/527; 436/532; 436/534; 436/823; 436/828
[58] Field of Search ............ 436/532, 823, 436/512, 527, 534, 501, 828; 530/391.1

[56] References Cited

U.S. PATENT DOCUMENTS

| | | | |
|---|---|---|---|
| 4,689,310 | 8/1987 | Kramer et al. | 436/532 |
| 4,716,122 | 12/1987 | Scheefers | 436/532 |
| 4,784,805 | 11/1988 | Blattner . | |
| 4,791,069 | 12/1988 | Hovorka et al. | 436/534 |
| 4,879,225 | 11/1989 | Morgan, Jr. et al. | 435/172.2 |

OTHER PUBLICATIONS

Foder, et al., Angewandte Chemie, 104:801 (1992) "Photolithographische Immobilisierung von Biopolymeren auf festen Tragern".

Sanger, et al., Bioconjugate Chem, 3:308 (1992) "Light–induced Coupling of Aqueos–Soluble Proteins to Liposomes Formed from Carbene Gen. Phospholipids".

Chong, et al., Jour. of Biological Chem., 256:5064–5070 (1981) "A New Heterobifunc. Cross–linking Reagent for the Study of Biol. Interactions between Proteins".

Ueno, et al., Biochem. Biophys. Res. Commun., 191:2, pp. 701–708 (1993).

*Primary Examiner*—Mary E. Ceperley
*Attorney, Agent, or Firm*—Brent A. Harris; Roche Diagnostics Corporation

[57] ABSTRACT

A biologically recognizing layer on a solid phase consisting of biologically recognizing molecules comprising regions which recognize a substance to be analyzed and regions which do not recognize a substance to be analyzed.

The biologically recognizing molecules are aligned on a suitably modified surface by means of molecular regions which do not recognize the substance to be analyzed. The biologically recognizing molecules are cross-linked with the aligning surface and are consequently covalently altered. The molecular regions recognizing the substance to be analyzed are not altered by the covalent bonding and retain their bonding activity.

The layer is produced in a novel two-stage method. In the first step, the biologically recognizing molecules, the aligning molecules and carrier molecules are adsorbed. In the second step, the molecules are covalently anchored by cross-linking. Cross-linking is brought about by photolytic activation of a water soluble reagent bonded to the carrier molecules.

15 Claims, 3 Drawing Sheets

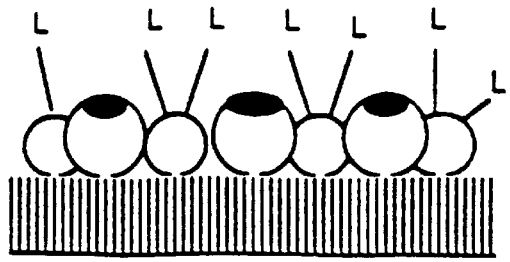

Fig. 1a

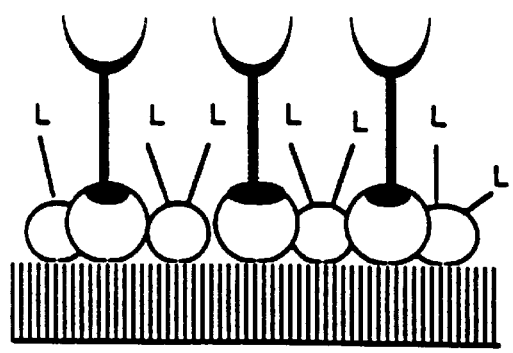

Fig. 1b

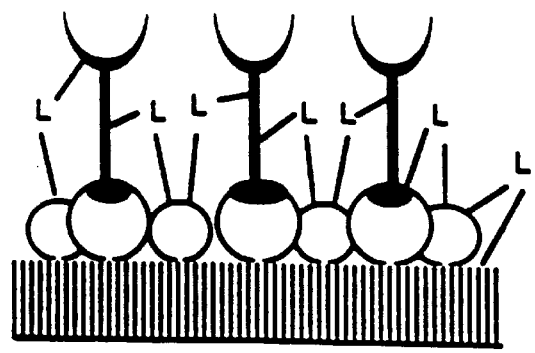

Fig. 1c

Definitions of Symbols Used in the Figures

| | |
|---|---|
| ▬ organic coating layer on solid surface | ⬤ aligning protein |
|  non-specifically adsorbing carrier molecule carrying crosslinking reagent L | Y recognizing biomolecule |
|  non-specifically adsorbing carrier molecule carrying crosslinking reagent L |  specifically adsorbing carrier molecule carrying crosslinking reagent L |

BIOSENSORY LAYERS

This is a continuation of application Ser. No. 08/492,257 filed Jun. 22, 1995, now abandoned which is a continuation of Ser. No. 08/085,716, Jun. 30, 1993 now abandoned.

FIELD OF THE INVENTION

The present invention relates to biologically recognizing layers immobilized on solid phases and to a method for the production of these layers.

DESCRIPTION OF RELATED ART

Solid phases comprising biologically recognizing layers are used in bioanalytical processes known as assay technology. Examples are enzyme immunoassays, fluorescence immunoassays or radiolimunoassays, depending on the method of labelling the molecules in question.

"Affinity sensors" have been described to an increasing extent for such detection methods. In contrast to the existing assay technology, these sensors can be used for direct detection without labelling and without washing and separation steps. These affinity sensors usually comprise a physical transducer, in particular a piezoelectric transducer [Anal. Chem. 63 (1991) 393 A] or an optical transducer [Sens. Actuators 4 (1983) 299; Thin Solid Films 126 (1985) 205; Biosensors and Biosensing 6 (1991) 215] or an electrochemical transducer [Biosensors & Bioelectronics 6 (1991) 55]), the sensor being closely linked to a biologically recognizing layer.

In assay technology, the biologically recognizing layer is frequently bonded to the solid phase by physical adsorption of the biologically recognizing molecules or molecule fragments to the solid phase surface. In contrast, because the sensor signal of the affinity sensors is directly proportional to a change in the surface occupation by adsorption or desorption of molecules, biologically recognizing layers in sensory analysis have more stringent bonding requirements. In sensory analysis, it is essential that the recognizing molecules are covalently bonded to the surface to prevent desorption of the recognizing molecules from the surface.

The sensitivity of detection and the dynamic range of these affinity sensors depend on the resolving power of the transducer to detect changes in surface coating, on the affinity of the recognizing layer for the substance to be detected, and on the bonding capacity of the surface for this substance. "Bonding capacity" means the number of active bonding sites per unit area.

The literature contains descriptions of various methods for covalently immobilizing biologically recognizing molecules on the surface. These methods usually involve biological or chemical modification of the molecules before immobilization.

Typical examples of covalent immobilization of antibodies or antibody fragments on an immunosensor include:

i) Oxidation of sugar radicals on the Fc part and immobilization of the antibodies via the resulting aldehyde groups on a surface containing complementary reactive groups in the form of hydrazine groups.

ii) Reaction of the resulting aldehyde groups with suitable biotin derivatives. Owing to the known high affinity of biotin for avidin and streptavidin, the thus-modified antibodies adhere extremely firmly to an avidin/streptavidin surface.

iii) Treatment of the antibodies with pepsin, reduction of the resulting Fab2 fragments to Fab' fragments and anchoring of the Fab' fragments by their free SH groups to a surface suitably equipped with functional groups (e.g. dithiopyridyl groups).

A disadvantage of the known methods is that chemical or biochemical modification of biologically recognizing molecules results in a substantial loss of activity. The present invention addresses these problems.

SUMMARY OF THE INVENTION

The present invention relates to an aligned, covalently immobilized layer of biologically recognizing unmodified molecules on a solid phase. The layer comprises a high density of active, specific bonding sites resulting in a high affinity and a high capacity to bond the molecule to be recognized.

The present invention also provides a novel method for the production of an aligned, covalently immobilized layer of biologically recognizing molecules which can be obtained even without chemical or biochemical modification for producing functional groups or covalent bonding to the recognizing molecule.

According to the invention, aligned covalent immobilization of biologically recognizing molecules is brought about by adsorbing the molecule to be immobilized, after suitable modification of the solid-phase surface, via the molecular regions which do not recognize the substance to be analyzed. This adsorption step is followed by covalent bonding via the regions which do not recognize the substance to be analyzed using specific "cross-linking" reagents which are particularly suitable for this immobilization process and which are introduced into the method via carrier molecules. The carrier molecules can be adsorbed or bonded to the surface of the solid phase before, during or after the aligned adsorption of the molecules which recognize the substance to be analyzed.

BRIEF DESCRIPTION OF THE DRAWINGS

FIG. 1 shows the co-immobilization of the carrier molecules with the aligning proteins on the solid phase surface.

FIG. 1a demonstrates the carrier molecules carrying the photoactivatable cross-linking reagent.

FIG. 1b shows the adsorption of the biologically recognizing molecule.

FIG. 1c demonstrates the cross-linking of the proteins with one another and with the surface.

FIG. 2 represents non-specific adsorption of the carrier molecules on the surface.

FIG. 3 is a diagrammatic illustration of specific adsorption of the carrier molecules on bonding sites of the aligning proteins.

DETAILED DESCRIPTION

Figure 2A:
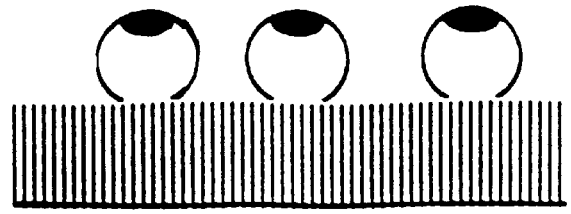
FIG. 2a shows the covalently immobilized aligning proteins.

The invention relates to a layer of recognizing molecules and a method of producing this layer on a solid phase surface, whereby unmodified, recognizing biomolecules, such as antibodies, receptors or DNA molecules, are immobilized on the surface in an aligned manner.

The method is applicable to all recognizing molecules comprising a region which recognizes a first substance to be analyzed and a second region which is efficiently separated in space from the first region and by means of which the recognizing molecule can be adsorbed onto a suitably modified surface.

These structural preconditions are satisfied in nearly all recognizing biomolecules. Ligand-recognizing receptors in the cell membrane, for example, comprise a hydrophilic part containing the ligand-recognizing region and also comprise a hydrophobic trans-membrane part. Physical adsorption of these receptors onto hydrophobic surfaces occurs via the trans-membrane part.

Antibodies comprise regions which recognize Fab parts with the antigen/hapten and also comprise the Fc part, which is unimportant to antigen/hapten recognition. By immobilization of molecules recognizing the Fc part, the surface of the solid phase can be shaped so that antibodies are directionally adsorbed on the surface via the Fc part.

In the case of DNA molecules, only a given sequence is used for recognition of a complementary strand. Sequences, for example of 3–10 bases, on a strand not used for recognition of the complementary strand, can be used for directional adsorption, if before adsorption, the aforementioned short portion of 3–10 bases is immobilized on the surface.

Finally, recognizing biomolecules have recently been produced in increasing quantities by genetic engineering. By these methods, the microorganism used for the production of the recognizing molecule can be so altered that additional regions, specifically suitable for adsorption to a surface, are synthesized at specific places on the recognition molecule.

In a preferred embodiment, the invention is an antigen-hapten-recognizing layer in which antibodies are covalently immobilized on the surface of a solid phase. The solid phase can be the surface of a physical transducer.

Directional adsorption of antibodies is brought about by first providing the surface of the solid phase with a monolayer of proteins having a specific affinity for the Fc part of antibodies. Protein A, protein G, Fc part-recognizing antibodies and antibody fragments or receptors are typical representatives of this class of proteins which, owing to their affinity for Fc parts of antibodies, are capable of aligning antibodies on a surface. The advantages of using this class of proteins are they have a number of bonding sites for the Fc part of antibodies and they take up considerably less space than the antibody which is subsequently analyzed. For example, protein A has four binding sites per molecule. Protein A also has a globular structure with a diameter of about 5 nm, compared with IgG-type antibodies with a separation of about 17 nm between antigen-recognizing regions.

By using this class of proteins a sufficiently high density of Fc-part specific bonding sites on the surface is obtained, even when the covalent immobilization of the protein on the surface is not directionally monitored.

There are a number of known methods for the immobilization of Fc-part recognizing proteins without monitoring the alignment on the surface. Usually, the surface of the solid phase is provided with a thin organic additional layer having a high density of functional groups (e.g. COOH or $NH_2$) suitable for immobilizing the proteins. The additional layer can be applied by silanization methods known from chromatography; by self-assembling methods from solution as described in recent literature; or from the gas phase by methods known as chemical vapor deposition, plasma induced chemical vapor deposition or plasma induced polymerization. Fc-part recognizing proteins are covalently immobilized by known affinity chromatography methods, by suitably activating the functional groups on the surface and subsequently reacting them with functional groups (e.g. $NH_2$ or COOH) on the protein.

Antibodies can then be directionally anchored to the surfaces, based on the affinity of the immobilized protein for the Fc part of the antibodies. It is known, however, that the affinity constants for these complexes (e.g. IgG protein A) are not usually sufficient to prevent desorption of the IgG molecule. In addition, various sub-classes of antibodies need special buffer conditions, such as high pH and high salt concentrations, before being bonded via their Fc part to the proteins. The antibodies rapidly become desorbed if there is a subsequent change of buffer to physiological conditions.

Therefore, directional adsorption has to be followed by a second step-covalent immobilization of the aligned molecules. This cross-linking process must not influence the antigen-bonding regions and the consequent activity of the antibodies. Conventional chemical methods of cross-linking usually have the disadvantage of being non-specific, that is cross-linking also occurs in the antigen/hapten-bonding regions and thus substantially reduces the activity of the antibodies.

The present invention addresses these concerns using a selective cross-linking technology comprising:

i) bifunctional reagents containing a water soluble photolytically activatable group and a chemically reactive group, together with ii) a method for photolytically-induced cross-linking in the regions which do not recognize the substance to be analyzed.

The cross-linking process, which results in surfaces on which antibodies are covalently and directionally immobilized, is based on the use of compounds having the general formula:

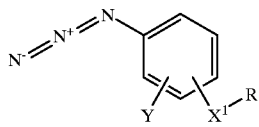

I wherein $X^1$ denotes a carbonyl (>C=O) or sulfonyl (>$SO_2$) group and Y=H, Y' or $X^1$-Y'. Y' is a hydroxy or alkoxy group (—O—Y") or an amino group (—NH—Y') and Y"=H or a water-solubilizing group of the type $(CH_2)_n A$. n=1–6.

A is a glycol or oligoethylene glycol substituent or a tertiary or quaternary amino group such as pyridyl, dialkylamino, N-alkyl pyridinium or trialkyl ammonium. Alkyl denotes a lower alkyl radical, approximately $C_1$–$C_4$.

The group R is a functional group having the general formula:

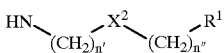

II wherein $X_2$ is a disulfide (—S—S—) or methylene (—$CH_2$-) group.

$R^1$ denotes an amino ($-NH-R^2-$) or carboxyl derivative ($-CO-R^3$). $R^2$=H or a derivatized carboxyakanoyl group ($-CO-(CH_2)_nCO-R^3$).

$CO-R^3$ is an activated carboxyl group such as e.g. an acid halide, imidazolide, hydrazide, anhydride, a carboxyl group derivatized with a dithiopyridyl group ($-NH-(CH_2)_{n'''}-S-S$-pyridyl) or a reactive ester with e.g. hydroxysuccinimide, isourea or hydroxysuccinimidesulfonic acid.

n', n", n'''=1–6.

If $X_2$ denotes a methylene group, $R^3$ can contain a disulfide group whereby $R^3$ denotes e.g. a cystamine derivative $-NH-(CH_2)2-S-S-(CH_2)_2-NH-R^2$, wherein $R^2$ has the significance given previously and the $R^3$ contained in $R^2$ does not contain a disulfide group.

When Y=H, $X^1$-R (without $R^3$) is hydrophilic (e.g. $X^1=SO_2$ or $R^1$=tert. amine or quaternary ammonium).

For hydrophiles $X^1$-R (without $R^3$), Y can optionally also be $X^1$-R (double anchoring).

The amino group $R^1$ can also be converted into other reactive groups such as an isocyanate, isothiocyanate, vinylsulfonic acid amide ($-NH-SO_2-CH=CH_2$), maleimide, halo-substituted triazinamino-, pyrimidinamino or pyridinamino compounds (e.g. dichlorotriazine), 2-halocarboxylic acid derivatives (e.g. with a 2-haloacetic acid halide, 2-halopropionic acid halide and the like), monoamides from dicarboxylic acid dihalides, epoxides, e.g. with epichlorohydrin or a cyclohexenedione derivative via Michael addition to a quinone.

antibodies subsequently bonded to the layer via the Fc part by the photolytically activatable cross-linking reagent before the photolytically induced cross-linking. The activity of the protein layer for bonding the Fc part of the antibodies would be drastically reduced by modification of the layer by the cross-linking reagent. In addition, when the antibodies to be immobilized are chemically modified by bonding the reagent in antigen-recognizing regions, antigen-hapten recognition is impaired.

In the present invention, chemical modification by the photolytically activatable cross-linking reagent of the immobilized proteins or of the antibodies to be immobilized is avoided by using a third species of molecule as carrier molecules (auxiliary molecules) for the photoreagent. These carrier molecules are externally reacted with the cross-linking reagent in such a manner that a number of photoactivatable groups are covalently bonded to a single carrier molecule. In this chemically modified form the carrier molecules are either immobilized on the surface of the transducer with the antibody-aligning proteins or are co-adsorbed on the protein surface with the antibodies to be immobilized. The present invention demonstrates that co-immobilization of these carrier molecules with the aligning proteins and the co-adsorption of the carrier molecules can be brought about without interfering with the adsorption of antibodies on the covalently immobilized protein layer.

The general properties required for the carrier molecules are:

i) a high solubility in water;

ii) the presence of a number of functional groups for the reaction with the photolytically activatable reagent, since

---

$X^1 = -CO-$
$X^1 = -SO_2-$
$X^2 = -S-S-$
$X^2 = -(CH_2)-$
$Y = -H$
$Y = -Y'$
$Y = -CO-Y' = -X^1-Y'$  $Y' = -O-Y"$  $Y" = -H$
$Y = -SO_2-Y' = -X^1-Y'$  $Y'= -NH-Y"Y" = -(CH_2)_n$-A $A = -O-(CH_2)_2-O-H$
$A = -O-[(CH_2)_2-O]_n-H$
$A = N(alkyl)_2$
$A = -N^+(alkyl)_3$
$A = $ -pyridine
$A = $ -pyridinium(N-alkyl)

$R^1 = -CO-R^3$      $R^2 = H$
$R^1 = -NH-R^2$      $R^2 = -CO-(CH_2)_n-CO-R^3$ $COR^3 = CO-Cl$
$COR^3 = CO-O$-acyl
$COR^3 = CO$-isourea
$COR^3 = CO-OSu$
$COR^3 = CO-OSu(SO3H)$
$COR^3 = CO-NH-NH_2$
$COR^3 = CO-NH-(CH_2)_{n'''}-S-S$-pyridyl
$COR^3 = CO-NHCONH_2$
$COR^3 = CO$-imidazolyl $X^2 = -CH_2-$,
$R^1 = COR^3 = CO-NH-(CH_2)_2-S-S-(CH_2)_2-NH-R^2$
($R^2 = H, CO-(CH_2)_n-CO-R^3$) whereby $R^3$ is as defined in column 3 with the exception of the disulfide compound
$R^1 = $ pyridinium(N$-CH_2-CO-R^3$)
$R^1 = $     $-N=C=O$
        $-N=C=S$
        $CH_2=CH-SO_2-NH-$
        -maleinimidyl
        $-NH-CO-CH(Cl)$-alkyl
        $-NH-CO$-alkylene$-CO-Cl$
        $-NHCH_2$-oxirane
        $-NH$-cyclohexenedione
        $-NH$-dichlorotriazinyl

---

The claimed method of the present invention of directional immobilization using the heterobifunctional reagents is applicable to surfaces onto which Fc part-recognizing proteins have been covalently immobilized. In this method, there is no modification of the protein layer nor of the cross-linking can occur only if a number of activatable groups are present on a molecule;

iii) the presence of functional groups for covalent cross-linking with the solid phase during co-immobilization;

iv) for co-adsorption, the presence of molecular regions which interact with the surfaces covered with proteins recognizing the Fc part.

Biomolecules which have these properties include albumins, polysaccharides or water-soluble synthetic polymers. The advantage of using these biomolecules is that the surfaces become insensitive to non-specific adsorption. The fact that efficient cross-linking occurs only if these carrier molecules contain a number of photo-activatable groups underlines the importance of the requirement for water-soluble (hydrophilic), bifunctional reagents in which the photo-activatable part of the molecule is soluble in water. If this requirement is not met, the modification will reduce the water solubility of the carrier molecules.

The co-immobilization of these carrier molecules is diagrammatically shown in FIG. 1.

First, the proteins to be aligned (e.g. protein A) and the carrier molecules (e.g. BSA) are co-immobilized, the carrier molecules already carrying the photo-activatable cross-linking reagents (L) (FIG. 1a).

Co-immobilization of the carrier molecules with the aligning proteins occurs by the same method used for immobilizing the aligning proteins. The relative concentration at the surface is adjusted via the concentration ratio of the two molecular species in solution.

The next step is adsorption of the antibody, the biologically recognizing molecule, as shown in FIG. 1b. The cross-linking of the proteins with one another and with the surface by photolytic activation of the cross-linking reagent (L) is symbolized by connecting lines in FIG. 1c.

For co-adsorption, the carrier molecules can be divided into two classes. A first class comprises carrier molecules which are non-specifically adsorbed on the surface and therefore mainly coat those parts of the surface which are not coated with proteins recognizing the Fc part. This class of carrier molecules is adsorbed on the surface before adsorption of the recognizing antibodies. Examples of this class are albumins, polysaccharides or water-soluble synthetic polymers.

FIG. 2 diagrammatically represents a directional covalent immobilization of native antibodies during non-specific adsorption of the carrier molecules on free bonding sites on the surface.

Figure 2B:
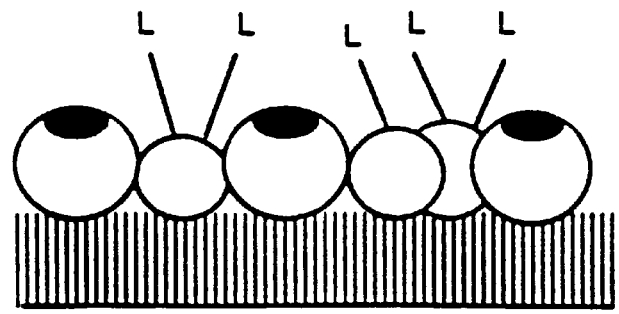
FIG. 2b shows the non-specific adsorption of the carrier molecules on free spaces between the covalently immobilized aligning proteins.
Figure 2C:
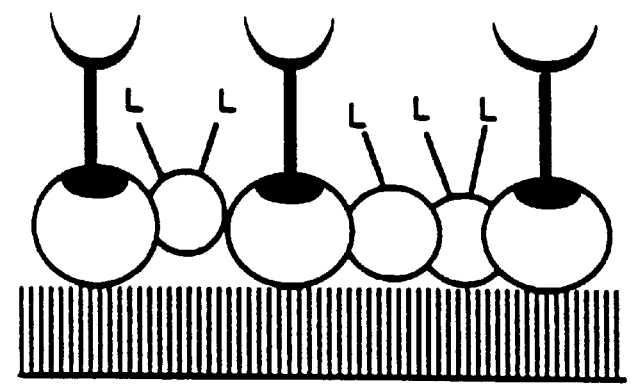
In FIG. 2c the biologically recognizing molecules are directionally adsorbed.
Figure 2D:
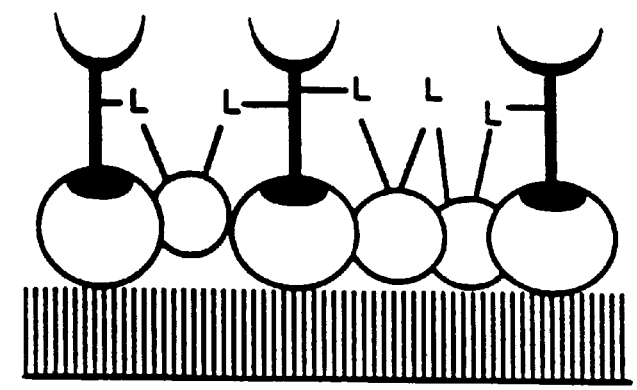
FIG. 2d represents the cross-linking of the proteins with one another and the surface.

FIG. 2a shows the covalently immobilized aligning proteins (e.g. protein A). In FIG. 2b, non-specific adsorption of the carrier molecules (e.g. BSA) is represented by circles marked with an L on free spaces between the covalently immobilized aligning proteins. Thereafter, the antibodies are directionally adsorbed (FIG. 2c). The connecting lines, as before, indicate cross-linking of the proteins between one another and with the surface (FIG. 2d).

A second class comprises carrier molecules which specifically coat Fc-bonding sites on the covalently immobilized protein layer. Fc fragments of antibodies are typical representatives of this class. These carrier molecules can be adsorbed on the surface simultaneously with the antibodies to be immobilized or after adsorption thereof. In the first case, the concentration ratio of carrier molecules (e.g. the Fc fragment) and recognizing antibodies must be very accurately adjusted to prevent an excessive number of Fc bonding sites being occupied by carrier proteins. If this occurs the result will be a reduction in the concentration of antigen-recognizing antibodies, thus reducing the sensitivity and dynamic range of the sensor.

In the case of subsequent adsorption of the carrier proteins (e.g. of the Fc fragment), saturation will be caused by these primary bonding sites which, due to three-dimensional geometry, are not accessible to the larger antibody molecules. However, these carrier proteins modified with cross-linking reagent are also capable of displacing adsorbed antigen-recognizing antibodies from the surface. Since this displacement is a slow process, it can be controlled via the incubation time using auxiliary proteins.

FIG. 3 is a diagrammatic illustration of directed covalent immobilization of native antibodies in the case of specific adsorption of carrier molecules on bonding sites of the aligning proteins.

Figure 3A:
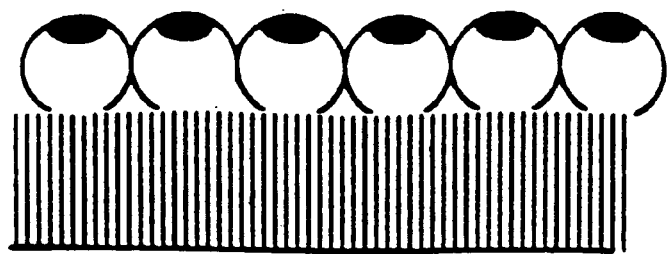
FIG. 3a illustrates covalently immobilized aligning proteins.

FIG. 3a illustrates covalently immobilized aligning proteins (e.g. protein A).

Figure 3B:
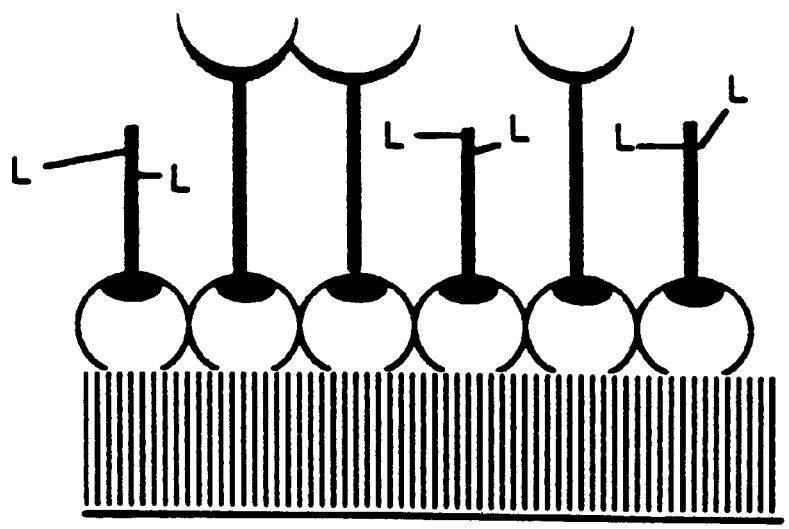
FIG. 3b shows specific coadsorption of the carrier molecules with the biologically recognizing molecules to the aligning proteins.

In FIG. 3b, specific co-adsorption of carrier molecules (e.g. Fc parts of antibodies) is indicated by bars marked L and attached to the aligning proteins. The antibodies are simultaneously adsorbed.

Figure 3C:
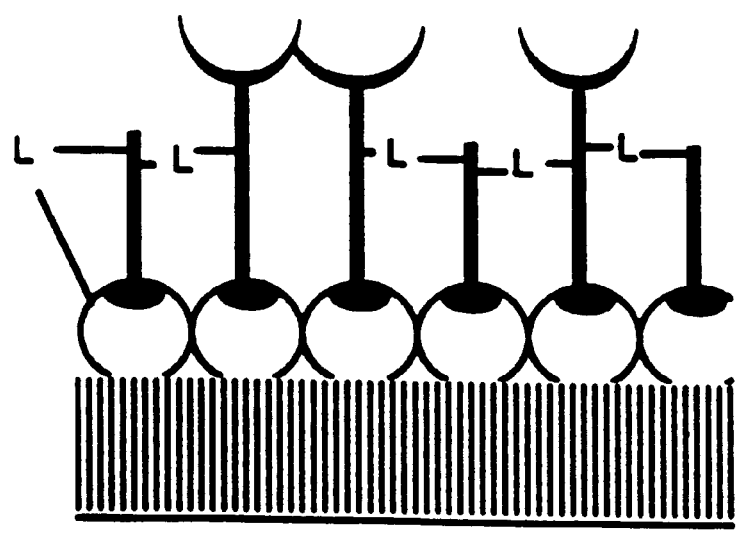
FIG. 3c illustrates the cross-linking of the proteins with one another and the surface.

The cross-linking of the proteins with one another and with the surface is indicated by connecting lines (FIG. 3c).

After co-adsorption of the antibodies to be immobilized and of the carrier proteins modified with the cross-linking reagent (or co-immobilization of the carrier proteins with the aligning protein), the proteins on the surface can be cross-linked with one another by irradiation. It is important for the photo-activatable part of the bifunctional cross-linking reagent to be water soluble. This high solubility in water is essential if the activator group (nitrene) is to project into the solution and thus experience intermolecular (not intramolecular) cross-linking. In the case of photolytically induced cross-linking, the irradiation time should be kept at a minimum in order to reduce the adverse effect on antibody activity of photolytically induced side-reactions such as photo-oxidation.

The following is an example of photochemical immobilization of anti HBsAg-(hepatitis B surface antigen) antibodies.

1. Silanization of the sensor surface

The sensor surface was silanized in known manner for 15 minutes in a dilute solution of octenyl trichlorosilane (0.5%) in hexadecane. The sensor surface was then thoroughly washed with hexadecane, hexane and ethanol in succession. The terminal double bonds on the silanized surface were oxidized to carboxylic acid groups in a solution of 2.5 mM potassium permanganate and 100 mM sodium periodate for at least 60 minutes. The reaction was stopped by immersing the sensor in a 100 mM sodium thiosulfite solution, after which the sensor surface was again thoroughly washed in water and ethanol. This method yielded monomolecular additional layers of high quality.

2. Immobilization of protein A

The carboxylic acid groups on the sensor surface were first activated and then converted into N-hydroxysuccinimide esters. Activation was brought about in a solution of 5% ethyl chloroformate and 4% pyridine in methylene chloride in a protective gas atmosphere for 1 hour. These activated carboxylic acid groups were converted into N-hydroxysuccinimide ester groups by incubating the sensor surface in a solution of 500 mM N-hydroxysuccinimide in pyridine. The sensor was then purified with ethanol and water and then dried.

Protein A was immobilized on the sensor surface by incubating the carrier in a solution of the protein (0.1 mg/ml) in 100 mM sodium citrate buffer, pH 4.8, for 1 hour. The protein was then washed with sodium citrate buffer and water.

3. Adsorption of BSA modified with photo-activatable reagent

A fixed amount of BSA in addition to the immobilized protein A can be adsorbed on a thus-prepared sensor surface.

The BSA was first modified with a photo-activatable reagent. For this purpose, 10 ml of a solution of BSA (10 mg/ml) in 1M ammonium sulphate buffer, pH 9.0, was provided and mixed with a solution of 7.5 mg of 6-(p-azidobenzenesulfonylamino)caproic acid N-hydroxysuccinimide ester in 100 µl of DMSO. The modification reaction lasted 15 minutes. The sensor surface was then brought into contact with the BSA solution for 30 minutes.

4. Adsorption of the antibodies and photochemical anchoring thereof 5 mg/ml of antibody was dissolved in 1M ammonium sulfate buffer, pH 9.0. The sensor surface was incubated in the solution for 30 minutes so that antibodies could be adsorbed on the protein A. The sensor surface was then washed with the same ammonium sulfate buffer and then coated therewith, followed by illumination with a mercury vapor lamp for 30 seconds. This process resulted in photochemical cross-linking of protein A, BSA and the Fc part of the antibody. The bonding sites of the antibodies remained intact. A sensor surface of this kind can be subjected to physiological buffer conditions without desorption of the antibodies.

The photo-activatable reagents were produced as follows.
General remarks

All compounds containing an azido group were additionally agitated with the exclusion of light.

HPLC was carried out at a flow rate of 1 ml/min. and detected by UV at 254 nm.

EXAMPLE 1

41 mg of N-(p-azidobenzenesulfonyl)-N'-(3-carboxypropionyl)-cystamine were stirred for 5 hours with 1 ml of thionyl chloride and then concentrated in a water-jet vacuum. The crude acid chloride was dissolved in 5 ml of THF and treated with 14 mg of N-hydroxysuccinimide in the form of a solution in 1 ml pyridine. The mixture was stirred for 2 hours and then concentrated in a high vacuum. 68 mg of N-(p-azidobenzenesulfonyl)-N'-(3-succinimidyloxycarbonyl-propionyl)cystamine were obtained in the form of the pyridinium salt.

The starting material used was prepared as follows:

2.2 g of cystamine dihydrochloride were dissolved in 20 ml of water and adjusted to pH 10 with NaOH. 2.1 g of p-azidobenzenesulfochloride were suspended in the solution and the mixture was stirred at room temperature for 5 hours. The precipitated N-(p-azidobenzenesulfonyl)cystamine was reacted with 2 g of succinic anhydride and stirred overnight. The resulting solution was acidified with HCl and the product was subsequently filtered off and washed with water. The residue was dried at room temperature in a high vacuum and gave 1.53 g of N-(p-azidobenzenesulfonyl)-N'-(3-carboxypropionyl)cystamine. The IR showed bands at 3283 (amide NH), 2134 (azide), 1714 (acid carbonyl), 1650 (amide), 1589+1547 (aromatic), 1284 (COOH), 1328+1180 (arylsulfonyl), 839 (p- disubst. benzene); TLC (silica gel: conc. $NH_3$ (EtOH=1%). Rf=0.7; m.p. 163° (dec.).

EXAMPLE 2

0.5 g of ε-(p-azidobenzenesulfonyl)aminocaproic acid was stirred with 5 ml thionyl chloride for 5 hours and then concentrated in a water-jet vacuum. The crude acid chloride was dissolved in 5 ml is of THF and treated with 348 mg of N-hydroxysuccinimide in the form of a solution in 5 ml of pyridine. The mixture was stirred for 2 hours and then concentrated in a high vacuum. There were obtained 1.09 mg of ε-(p-azidobenzenesulfonylamino)caproic acid N-hydroxy-succinimide ester in the form of the pyridinium salt.

The starting material used was prepared as follows:

4.57 g of ε-aminocaproic acid were dissolved in a solution of 8.8 g of $NaHCO_3$ in 100 ml water. 7.6 g of p-azidobenzenesulfonic acid chloride were suspended therein and the mixture was stirred overnight. The product was precipitated from the resulting solution with HCl, filtered off and washed with water. 4.56 g of ε-(p-azidobenzenesulfonylamino)caproic acid were obtained after drying in a high vacuum at room temperature. The IR showed the expected bands at 2907 (azide), 1715 (acid carbonyl), 1585+1400 (aromatic), 1282 (COOH), 1319+1153 (aryl sulfonyl), 834 (p- disubst. benzene); TLC (silica gel: EtOAc)/EtOH=3) Rf=0.55; m.p.=126–127° C.

ε-(p-Azidobenzenesulfonylamino)caproic acid prepared in a similar manner showed the same running behaviour in the TLC and melted at 132–133°. It can be converted into ε-(p-azidobenezene-sulfonylamino)caproic acid N-hydroxysuccinimide ester according to Example 6.

EXAMPLE 3

31 mg of ε-(p-azidobenzenesulfonyl)aminocaproic acid were stirred with 1 ml of thionyl chloride for 5 hours and then concentrated in a water-jet vacuum. The crude acid chloride was dissolved in 5 ml of THF and treated with 22 mg of N-hydroxy-succinimide-2-sulfonic acid in the form of a solution in 1 ml of pyridine. The mixture was stirred for 2 hours and then concentrated in a high vacuum. There were obtained 58 mg of ε-(p-azidobenzene-sulfonyl) aminocaproic acid (N-hydroxysuccinimide-2-sulfonic acid) ester in the form of the dipyridinium salt.

The starting material used was prepared according to Example 2.

EXAMPLE 4

550 mg of ε-(p-azidobenzoyl)aminocaproic acid were dissolved in 5 ml of THF and 0.5 ml of thionyl chloride was added. The mixture was stirred for 5 hours and then concentrated. The crude acid chloride was dissolved in 5 ml of THF, treated with 251 mg of 2-(2-amino-ethyldithiopyridine) in 2 ml pyridine and the mixture was stirred for an additional 2 hours. 20 g of ice were added, the pH was adjusted to 6 with NaOH and 6 g of NaCl were added. The mixture was stirred for 1 hour, then filtered, washed with saturated sodium chloride solution and dried in a high vacuum (room temperature). TLC (silica gel: conc. HCl/EtOH=1%) Rf=0.2; TLC (silica gel—EtOAc) Rf=0.6

EXAMPLE 5

280 mg of ε-(p-azidobenzoyl)aminocaproic acid N-hydroxy-succinimide ester were dissolved in 5 ml of THF and added dropwise to a solution of 140 mg of hydrazinium monochloride in 20 ml of water. The mixture was made basic with an excess of soda and then filtered. The residue was washed with water and dried in a high vacuum. There were obtained 305 mg of ε-(p-azidobenzoyl)-aminocaproic acid hydrazide. TLC (silica gel: conc. HCl/EtOH=1%) Rf=0.7; TLC (silica gel: conc. $NH_3$/EtOH=1%) Rf=0.8.

EXAMPLE 6

100 mg of 6-(3-azido-5-sulfobenzoylamino)hexanoic acid (0.28 mmol) were dissolved in 2 ml of dry THF at room temperature, treated dropwise with 0.7 ml of thionyl chloride while stirring and the mixture was then stirred overnight at room temperature (magnetic stirrer). The excess thionyl chloride and the solvent were then removed in a water-jet vacuum (CaCl tube) and the residue was stirred twice (magnetic stirrer, water-jet vacuum) with 2 ml of THF each time in order completely to remove the thionyl chloride. The yellowish residue was dissolved in 2 ml of THF, 35 mg of N-hydroxysuccinimide in 1 ml of THF were added to the solution and, after the addition of 200 mg of finely pulverized sodium hydrogen carbonate, the mixture was stirred at room temperature for 24 hours. After removal of the solid at the bottom, the yellowish solution was concentrated at room temperature in a water-jet vacuum. Ethyl acetate was added in order to separate the product, 6-(3-azido-5-sulfobenzoylamino)hexanoic acid N-hydroxysuccinimide ester as a yellowish powder (about 70 mg), which was dried in a high vacuum at room temperature. IR (KBr;cm$^{-1}$): 3420 (amide-NH), 2114 (azide), 1737 (ester carbonyl), 1658 (amide carbonyl), 1589 (aromatic), 1541 (amide-2 bands), 1195 (sulfonate). TLC (silica gel: ethanol-NH$_3$): Rf product=0.8, Rf educt=0.6, Rf hydroxysuccinimide=0.05.

The starting material used was prepared as follows:

14.6 g of 3-nitro-5-sulfobenzoic acid monosodium salt were dissolved in 300 ml of pyridine and stirred for 2 hours, after which 2.2 ml of oxalyl chloride were added dropwise. After 1 hour, 16.6 g of benzyl ε-aminocaproate as a solution in 100 ml of THF were added dropwise and the mixture was stirred overnight. The mixture was concentrated on a rotary evaporator and then stirred with 100 g of strongly acid ion exchanger in 100 ml water for 50 hours. The mixture was filtered and washed with water, and the filtrate was concentrated. The residue was dissolved in 30% methanol/water, treated with 21 g of tetraethylammonium bromide and adjusted to pH 6.5 with sodium hydroxide solution. The resulting solution was chromatographed on 500 g of silanized silica gel (RP2) with 30% methanol. 8.6 g of benzyl ε-(3-nitro-5-sulfobenzoylamino)caproate were obtained in the form of the tetraethylammonium salt, which was stirred with 100 g of cation exchanger in water, filtered off and washed with water. The filtrate was concentrated and gave the corresponding free sulfonic acid. TLC (silica gel: HOAc/EtOAc=20%) Rf=0.7 (educt=0.4); TLC (silica gel: NH$_3$/EtOH=1%) Rf=0.8 (educt=0.7); TLC (RP18: EtOH/ Et$_4$N$^+$ (0.01M) phosphate buffer (0.1M; pH 6.5)=60% Rf=0.4 (educt=0.8). HPLC (RP18: MeCN/Et$_4$N$^+$ (0.01M) phosphate buffer (0.1M; pH 6.5)=30%) t$_R$=5.9 min. (educt= 1.3 min). 1.32 g of benzyl 6-(3-nitro-5-sulfobenzoylamino) hexanoate were dissolved in 30 ml ethanol/water=60%, 100 mg of Pd/C 10% were added and the mixture was hydrogenated while stirring (magnetic stirrer). The total absorption of hydrogen (1.5 hours) was 235 ml. TLC control showed that starting material was no longer present. In the TLC the amine is present practically at the start. The catalyst was filtered off and the solution was concentrated to dryness on a rotary evaporator. The IR control of the substance showed the complete absence of the original nitro group and of the benzyl group. The resulting 6-(3-amino-5-sulfobenzoylamino)hexanoic acid was used directly for the preparation of the azide.

About 1.0 g of 6-(3-amino-5-sulfobenzoylamino) hexanoic acid=about 3.0 mmol was dissolved in 15 ml of water and 3 ml of THF, 1 ml of conc. HCl was added and the solution was cooled to 0°. Then, 210 mg of sodium nitrite in 1.5 ml of water were added dropwise at 0°. After completion of the dropwise addition a fine precipitate formed (diazonium salt); it was stirred at room temperature for 1 hour. Then, 208 mg of sodium azide in 1 ml of water were slowly added dropwise (evolution of gas, foaming; suspension passed into solution). The exchange with sodium azide proceeded rapidly; after 1 hour TLC showed the azide only, without any amine. TLC with silica gel: ethanol/HCl: Rf (azide): about 0.6; Rf (amine): about 0.5; amine fluoresces, azide adsorbs. The azide spot is brown under UV light. The azide solution was concentrated completely in a high vacuum while stirring at room temperature yielding a crystalline and yellowish powder. IR control: all required IR bands for 6-(3-azido-5-sulphobenzoylamino)hexanoic acid present and correct.

EXAMPLE 7

β-(3-azido-5-sulfobenzoylamino)propionic acid was converted into the N-hydroxysuccinimide ester according to Example 6.

The starting material used was prepared as follows:

14.6 g of 3-nitro-S-sulfobenzoic acid monosodium salt were dissolved in 300 ml of pyridine and stirred for 2 hours, then 2.2 ml of oxalyl chloride were added dropwise. After 1 hour 13.6 g of β-alanine tert. butyl ester were added and the mixture was stirred overnight. The mixture was concentrated on a rotary evaporator and then stirred with 100 g of strongly acid ion exchanger in 100 ml of water for 16 hours. The mixture was filtered, washed with water and the filtrate was concentrated. The residue was dissolved in 30% methanol/water, 21 g of tetraethylammonium bromide were added and the pH was adjusted to 6.5 with sodium hydroxide solution. The resulting solution was chromatographed on 1 kg of silanized silica gel (RP2) with 30% methanol. About 6 g of β-3-nitro-S-sulfobenzoyl)aminopropionic acid were obtained in the form of the tetraethylammonium salt, which was stirred with 100 g of cation exchanger in water and, after filtration, washed with water. The filtrate was concentrated to give the corresponding free sulfonic acid. TLC (silica gel: HOAc/EtOAc) Rf=0.5 (byproduct: diamide=0.9).

The conversion of the nitro group by reduction to the amino group and Sandmeyer reaction to the azide group were carried out analogously to Example 6.

EXAMPLE 8

8.6 g of N-(3-azido-5-sulfobenzoyl)-N'-(3-carboxypropionyl)-ethylenediamine were dissolved in 50 ml of THF, treated with 10 ml of thionyl chloride and stirred for 5 hours. The mixture was concentrated and the residue (crude acid chloride) was dissolved in 50 ml of THF and treated in succession with of 2 g of N-hydroxy-succinimide as a solution in 10 ml of THF and 10 g of sodium bicarbonate. The mixture was stirred overnight, filtered, the residue was washed with THF and the filtrate was then concentrated and the residue was dried in a high vacuum at room temperature. TLC (silica gel: conc. NH$_3$/EtOH=1%) Rf=0.8.

The starting material used was prepared as follows:

12 g of 3-nitro-5-sulfobenzoic acid monosodium salt were stirred with 200 ml of pyridine for 2 hours and then treated with 8.8 g of thionyl chloride. After 1 hour 24 g of ethylenediamine were added dropwise and the mixture was stirred overnight. The mixture was then concentrated, the residue was dissolved in THF, treated in succession with 10 g of succinic anhydride and 20 g of soda and the mixture was again stirred overnight. The mixture was filtered, washed with THF, the filtrate was concentrated and the residue was used in the next stage. 3310+3255 (amine), 1730 (acid carbonyl), 1640+1506 (aromatic), 1640+1539 (amide), 1296 (arylsulfonyl), TLC (silica gel: conc. HCl/EtOH=1%) Rf=0.5; TLC (silica gel: conc. NH$_3$/EtOH=1%) Rf=0.6; HPLC (10% MeCN-RP18): t$_R$=1.7 min. (t$_R$intermediate=3.3 min./t$_R$ educt=3 min).

N-(3-Amino-5-sulfobenzoyl)-N'-(3-carboxypropionyl) ethylene-diamine was dissolved in 12 ml of hydrochloric acid (37%) and 100 ml of water, treated dropwise at 0° with sodium nitrite solution (4N) and stirred at this temperature for 1 hour (showed reaction with KI/starch and with alkaline 2-naphthol solution). Then, 13 g of sodium azide were added slowly, the mixture was stirred at room temperature for a further 5 hours, 20 g of NaCl were then added, the mixture was stirred for 1 hour and filtered. The residue was washed with saturated sodium chloride solution and dried at room temperature in a high vacuum. The crude product was characterised by IR and was used directly in the next step. 2121 (azide), 1736 (acid carbonyl), 1507 (aromatic), 1640+ 1507 (amide), 1180 (arylsulfonyl), 857 (p-disubst. benzene).

EXAMPLE 9

15 g of 2-(p-azidobenzoylaminomethyl)pyridine were dissolved in 50 ml of THF, treated with 50 g of 2-bromoacetyl bromide at -20° C. and left to stand at the same temperature overnight. The mixture was concentrated and the residue was dissolved in 50 ml of THF. 11.5 g of N-hydroxysuccinimide were added, the mixture was stirred at room temperature overnight and then concentrated. There was thus obtained N-(succinimidyloxycarbonylmethyl)-2-(p-azidobenzoyl-aminomethyl)pyridine.

Alternatively, 15 g of 2-(p-azidobenzoylaminomethyl) pyridine were dissolved in 500 ml of water, treated with 10 g of 2-chloroacetic acid and stirred overnight. 100 g of NaCl were added, the mixture was stirred for 1 hour, filtered, the residue was washed with saturated sodium chloride solution and dried in a high vacuum. There was obtained N-carboxymethyl)-2-(azidobenzoylaminomethyl)pyridine which showed the following bands in the IR: 3427+3283 (amide-NH), 2121 (azide), 1633+1565 (amide) 1499+1601 (aromatic), 859 (p-disubst. benzene), 710+763 (monosubst. benzene).

The compound can be converted according to Example 6 into the previously described N-(succinimidyloxycarbonylmethyl)-2-(p-azidobenzoylaminomethyl)pyridine.

The starting material was prepared as follows:

14.3 g of p-azidobenzoic acid were suspended in 100 ml of thionyl chloride and stirred for 5 hours (a solution resulted). The mixture was concentrated, the residue was dissolved in 50 ml of THF, 30 ml of 2-aminomethylpyridine were added and the mixture was stirred at room temperature for 2 hours. The mixture was then poured onto 200 g ice, neutralized with NaOH, filtered, washed with water and dried in a high vacuum. The IR showed bands at 3306 (amide-NH), 2125 (azide), 1626+1547 (amide), 1500+1603 (aromatic), 852 (p-disubst. benzene), HPLC (RP18.30–100% MeCN in 20 min.) $t_R$=8 min. ($t_R$ educt=10 min). TLC (silica gel: HOAc/EtOAc=20%), Rf=0.2.

EXAMPLE 10

5-Azidoisophthaloyl dichloride was freshly prepared from 2.5 g of 5-azidoisophthalic acid and was reacted in crude form with a solution of 5.2 g ε-aminocaproic acid in 100 ml of water and 10 g of soda. After stirring for 5 hours the resulting solution was acidified with HCl, then filtered and washed with water. The residue consisting of 3,5-di(6-capronylamino)azidobenzene was dried and characterized by IR: 3460 (amide-NH), 2121 (azide), 1717+1559 (amide), 1599+1631 (aromatic). The carboxylic acid groups were activated according to Example 6.

We claim:
1. A biomolecular coated solid phase surface composition for use in biosensory assays, comprising:
an organic layer applied to the solid phase surface, wherein the organic layer has a high density of functional COOH or $NH_2$ groups suitable for immobilizing aligning proteins and carrier molecules;
a layer of aligning proteins and of modified carrier molecules covalently bound to the organic layer, wherein said aligning proteins have an affinity for a non-recognizing part of a recognizing biomolecule, and said modified carrier molecules are carrier molecules externally reacted with a cross-linking reagent, said carrier molecules having a photoreactive phenylazido group for cross-linking the biomolecules to one another, said modified carrier molecules selected from the group consisting of albumins, polysaccharides and water soluble synthetic polymers; and
a layer of said recognizing biomolecules immobilized via the aligning proteins on the surface wherein the non-recognizing part of the recognizing biomolecules is affinity bound to the aligning proteins and covalently bound to the modified carrier molecules via the phenylazido group and the recognizing part of the biomolecules remains essentially unaltered by said covalent bonding and is oriented away from the solid phase surface.
2. The composition of claim 1, wherein the cross-linking reagent is of the formula

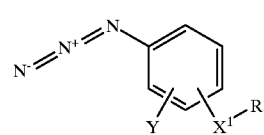

I wherein $X^1$ is a carbonyl (>C=O) or sulfonyl (>SO$_2$) group; Y=H, Y' or $X^1$—Y'; Y' is selected from the group consisting of hydroxy, an alkoxy group (—O—Y'') and an amino group (—NH—Y''); Y''=H or a water-solubilizing group $(CH_2)_nA$; n=1–6;
A is a glycol or oligoethylene glycol substituent or a tertiary or quaternary amino group selected from the group consisting of pyridyl, dialkylamino, N-alkyl pyridinium and trialkyl ammonium; alkyl denotes a lower alkyl radical, $C_1$–$C_4$;
R is a functional group of the formula

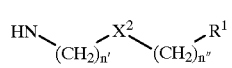

II wherein $X_2$ is a disulfide (—S—S—) or methylene (—CH$_2$—) group;
$R^1$ is selected from the group consisting of an amino (—NH—$R^2$), carboxyl derivative (—CO—$R_3$), $R^2$=H and a derivatized carboxyalkanoyl group (—CO—$(CH_2)_n$CO—$R^3$);
CO—$R^3$ is an activated carboxyl group wherein the activated carboxyl group is selected from the group consisting of an acid halide, imidazolide, hydrazide, anhydride, a carboxyl group derivatized with a dithiopyridyl group (—NH—$CH_2)_{n'''}$—S—S-pyridyl) and a reactive ester with hydroxysuccinimide, isourea or hydroxysuccinimidesulfonic acid; and n', n'', n'''=1–6.

3. The composition of claim 1, wherein the cross-linking reagent contains water soluble groups selected from the group consisting of sulfonic acid, carboxylic acid, an hydroxyl group, tertiary amino and quartenary ammonium group which are located either on a spacer between the chemically reactive group and the photoactivatable group or on the photoactivatable group.

4. A biomolecular coated solid phase surface composition for use in biosensory assays, comprising:

an organic layer applied to the solid phase surface, wherein the organic layer has a high density of functional COOH or $NH_2$ groups suitable for immobilizing aligning proteins;

a layer of aligning proteins covalently bound to the organic layer, wherein said aligning proteins have an affinity for a non-recognizing part of a recognizing biomolecule;

a layer of modified carrier molecules and recognizing biomolecules bound to the aligning proteins, wherein said modified carrier molecules are carrier molecules externally reacted with a cross- linking reagent, said carrier molecules having a photoreactive phenylazido group for cross-linking the biomolecules to one another, said carrier molecules selected from the group consisting of albumins, polysaccharides and water soluble synthetic polymers; and wherein the nonrecognizing part of the recognizing biomolecules is affinity bound to the aligning proteins and covalently bound to the modified carrier molecules via the phenylazido group and the recognizing part of the biomolecules remains essentially unaltered by said covalent bonding and is oriented away from the solid phase surface.

5. The composition of claim 4, wherein the cross-linking reagent is of the formula

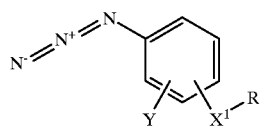

I wherein $X^1$ is a carbonyl (>C=O) or sulfonyl (>$SO_2$) group; Y=H, Y' or $X^1$-Y'; Y' is selected from the group consisting of hydroxy, an alkoxy group (—O—Y") and an amino group (—NH—Y"); Y"=H or a water-solubilizing group $(CH_2)_nA$; n=1–6;

A is a glycol or oligoethylene glycol substituent or a tertiary or quaternary amino group selected from the group consisting of pyridyl, dialklamino, N-alkyl pyridinium and trialkyl ammonium; alkyl denotes a lower alkyl radical $C_1$–$C_4$;

R is a functional group of the formula

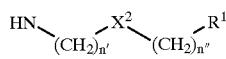

II wherein $X_2$ is a disulfide (—S—S—) or methylene (—$CH_2$—) group;

$R^1$ is selected from the group consisting of an amino (—NH—$R^2$), carboxyl derivative (—CO—$R_3$), $R^2$=H and a derivatized carboxyalkanoyl group (—CO—$(CH_2)_nCO$—$R^3$);

CO—$R^3$ is an activated carboxyl group wherein the activated carboxyl group is selected from the group consisting of an acid halide, imidazolide, hydrazide, anhydride, a carboxyl group derivatized with a dithiopyridyl group (—NH—$CH_2$)N'''—S—S-pyridyl) and a reactive ester with hydroxysuccinimide, isourea or hydroxysuccinimidesulfonic acid; and n', n", n'''=1–6.

6. The composition of claim 4, wherein the cross-linking reagent contains water soluble groups selected from the group consisting of sulfonic acid, carboxylic acid, an hydroxyl group, a tertiary amino and a quartenary ammonium group which are located either on a spacer between the chemically reactive group and the photoactivatable group or on the photoactivatable group.

7. The composition of claim 4, wherein the aligning proteins are proteins having a specific affinity for Fc parts of antibodies.

8. The composition of claim 7, wherein the recognizing biomolecules are antibodies.

9. The composition of claim 8 wherein the carrier molecules specifically bind to Fc parts on the aligning proteins.

10. A method of producing a biomolecular coated solid phase surface composition for use in biosensory assays, comprising:

(a) coating the solid phase surface with an organic layer having a high density of functional COOH or $NH_2$ groups;

(b) covalently immobilizing aligning proteins to the organic layer, said aligning proteins having an affinity for a nonrecognizing part of a recognizing biomolecule and having functional groups for covalent binding to the organic layer located so as not to interfere with said affinity;

(c) applying a layer of modified carrier molecules, said carrier molecules selected from the group consisting of albumins, polysaccharides and water-soluble synthetic polymers, having a photoactivatable phenylazido group for cross linking biomolecules, by (i) coimmobilizing the modified carrier molecules to the organic layer with the aligning proteins of step (b) by absorptive or covalent binding of said carrier molecules to the organic layer simultaneous with, or immediately subsequent to, the immobilization of the aligning proteins, in such manner that the phenylazido group is available for cross-linking, or (ii) binding the modified carrier molecules by affinity binding to the biomolecule recognition site of the immobilized aligning proteins;

(d) absorbing recognizing biomolecules having a recognizing part for recognizing an analyte, to the immobilized aligning proteins through the nonrecognizing part of the recognizing biomolecules; and (e) covalently immobilizing the absorbed recognizing biomolecules to one another and to the aligning proteins by means of photolytically induced crosslinking through the photoactivatable phenylazido groups of the modified carrier molecules, whereby the recognizing part of the biomolecules remains essentially unaltered by said covalent immobilization and is oriented away from the solid phase surface.

11. The method of claim 10, wherein the cross-linking reagent is of the formula

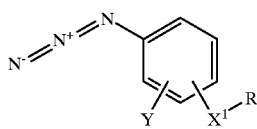
I wherein $X^1$ is a carbonyl (>C=O) or sulfonyl (>SO$_2$) group; Y=H, Y' or $X^1$-Y'; Y' is selected from the group consisting of hydroxy, an alkoxy group (—O—Y''') and an amino group (—NH—Y'''); Y'''=H or a water-solubilizing group $(CH_2)_nA$; n=1–6;

A is a glycol or oligoethylene glycol substituent or a tertiary or quaternary amino group selected from the group consisting of pyridyl, dialkylamino, N-alkyl pyridinium and trialkyl ammonium; alkyl denotes a lower alkyl radical, $C_1$–$C_4$;

R is a functional group of the formula

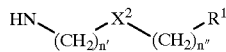
II wherein $X_2$ is a disulfide (—S—S—) or methylene (—CH$_2$—) group;

$R^1$ is selected from the group consisting of an amino (—NH—$R^2$), carboxyl derivative (—CO—$R_3$), $R^2$=H and a derivatized carboxyalkanoyl group (—CO—(CH$_2$)$_n$CO—$R^3$);

CO—$R^3$ is an activated carboxyl group wherein the activated carboxyl group is selected from the group consisting of an acid halide, imidazolide, hydrazide, anhydride, a carboxyl group derivatized with a dithiopyridyl group (—NH—CH$_2$)$_{n'''}$—S—S-pyridyl) and a reactive ester with hydroxysuccinimide, isourea or hydroxysuccinimidesulfonic acid; and n', n'', n'''=1–6.

12. The method of claim 10, wherein the modified carrier molecules are prepared by reacting a carrier molecule with a water soluble crosslinking reagent, said reagent having a chemically reactive group for reacting with functional groups on the carrier molecule, and a photoactivatable phenylazido group.

13. The method of claim 10, wherein the recognizing biomolecules are antibodies, and wherein the antibodies are directionally absorbed through their Fc part to the immobilized aligning proteins.

14. The method of claim 13, wherein the aligning proteins are proteins having a specific affinity for the Fc part of antibodies.

15. The method of claim 14, wherein the carrier molecules specifically absorb to Fc bonding sites of the immobilized aligning proteins with or after the absorption of the antibodies.

* * * * *